United States Patent [19]

Taylor

[11] Plant 4,974

[45] Jan. 18, 1983

[54] APPLE TREE

[75] Inventor: Alvah Taylor, Selah, Wash.

[73] Assignee: McCormick Fruit Tree Co., Yakima, Wash.

[21] Appl. No.: 281,426

[22] Filed: Jul. 8, 1981

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

An apple tree which is a sport of "Starkspur Red Rome Beauty" (U.S. Plant Pat. No. 3,121) and develops overall red fruit coloring in September well in advance of parent, has greater sugar content, keeps well in ordinary storage conditions on the average about one hundred sixty days or longer, is mildew and insect resistant similarly as parent, but grows as a less compact tree than parent.

3 Drawing Figures

My present invention relates to a new variety of apple tree discovered by me as a sport in a cultivated orchard in a group of about one hundred fifty "Starkspur Red Rome Beauty" apple trees (U.S. Plant Pat. No. 3,121), being a section of my orchard in which that "Starkspur" variety had been growing for some time, and which new variety is identified by me as the Taylor Strain relating to the Red Rome Beauty general designation.

The variety of my new development, was discovered in the vicinity of Selah, Wash., and was particularly attractive because of its color, and I have therefore chosen to designate the same as "Flamespur" Red Rome, Alvah Strain.

My new variety was noticed by me as a tree, in the early fall when the fruit ripened, because of the fact that the fruit on the tree was solid red overall in contrast to the usual Red Rome which is about half colored being green on the backside, at the time my new variety is ready to harvest.

My new variety is ready to harvest about twenty days earlier than "Starkspur" and in addition my new variety has other distinguishing characteristics as compared with "Starkspur" including the fact that the fruit contains at least one percent more sugar on the average.

Other identifying characteristics of my new variety include the pressure rating of twenty pounds and that the tree itself is not as compact as "Starkspur".

From the foregoing it will be understood that the several improved characteristics of my new variety, are in fact valuable distinctions for an apple tree, including but not limited to the following:

1. Distinctive overall red color earlier than parent, about twenty days.
2. Early harvest potential.
3. Increased sugar content. (about 1% on the average)
4. Good keeping in ordinary storage. (about 160 days)
5. Dessert quality as well as usual culinary aspects.
6. Resistant to mildew as parent.
7. Somewhat less compact tree size than "Starkspur" parent.

I have asexually reproduced my new variety of apple tree by grafting and find that the aforesaid characteristics come true in successive propagations, supporting the improved commercial attraction of my new variety, and identifiable by the detailed description supplied, taken in conjunction with the drawing. This shows in color certain of the described aspects although the color of the leaves in the middle view is not completely true. Otherwise the colors are as nearly true as possible to create in color reproductions of the kind supplied, reference being had to the Nickerson Color Fan published by Munsell Color Company for identifying terminology.

Where ordinary descriptive color terms are applicable, they are used.

Locality where grown and observed: Selah, Wash.

Date of first picking: September 20.

Tree: Medium size; medium vigor; spreading; dense; round form; hardy, rapid growing; very productive; regular bearer.

*Trunk.*—Stocky; medium.

*Branches.*—Thick; smooth; much-branched. Color — Brown 10 YR 4/4. Lenticels — Few and small.

Foliage:

*Leaves.*—Medium (about 4 4/10" long — 2" wide); oval; taper-pointed; medium thickness. Color — Dark green 5 G 4/3. Margin — Crenate; finely serrate. Petiole — Length (1 2/10"); slender.

Flowers:

*Dates of first and full bloom.*—About May 3 and May 8 respectively.

*Size.*—Medium.

*Color.*—White.

*Blooming.*—Late as compared with other varieties.

Fruit:

*Maturity when described.*—Eating hard, September 20.

*Size.*—Uniform. Axial diameter 3.6 inches. Transverse 3.1 inches.

*Form.*—Uniform; symmetrical; regular; round.

*Cavity.*—Symmetrical. Depth — About 7/10 inches. Breadth — About 1 inch.

*Basin.*—Symmetrical; rounded; wide base; even; glabrous.

*Stem.*—Stout; glabrous. Length — 1 and 2/10 inches. Bracts — few; usually one.

*Calyx.*—Closed; persistent; broadly acute; Length — 4/10 inches. Separated; erect; inner and outer surfaces glabrous.

*Eye.*—Medium; closed.

*Skin.*—Thick; tough; smooth; glossy; waxed. Dots — Obscure; few; small; even. Color — Pinkish white. Distribution — Sparse. Ground color — None to 5-R 3. Color markings — Blushed; bright. Bloom — Wanting. General color effect — Dark red 5-R all over.

Flesh: Juicy; satiny.

*Color.*—White.

*Texture.*—Hard; fine; crisp.

*Flavor.*—Acid; sweet; rich.

*Aroma.*—Faint.

*Quality.*—Best.

Core:

*Sessile.*—Medium.

*Bundle area.*—Medium (longitudinal section). Ovate; symmetrical. Halves of area — Equal. Bundles — Yellowish; two whorls. Alternate bundle — Below. Core lines — Meeting. In cross-section — Distinct. Carpellary area — Distinct; large.

*Calyx.*—Pubescent; narrow. Stem of funnel — Short. Depth of tube to shoulder 4/10 inch. Entire depth — 6/10 inch. Styles — Fleshy at base; distinct; pubescent throughout.

*Stamens in one.*—Distinct.

*Auxillary cavity.*—Present.

*Seed cells.*—Closed.

*Cell walls.*—Thick; tough. Length — 8/10 inch. Breadth — 4/10 inch. Longitudinal section — Broadly oblong; acute. Surface — Smooth. Cross-section — Broad.

Seeds:

*Number perfect.*—12.

*Number imperfect.*—0.

*Largest number in one cell.* —3.

*Length.*—0.035 inch.

*Breadth.*—0.020 inch.

*Color.*—5 YR 4/5.

Use: Market; dessert; culinary.

Keeping quality: Good; about 160 days or longer.

Resistance to: Insects and diseases good; mildew resistant in a similar manner to Starkspur Red Rome Beauty.

I claim:

1. A new and distinct variety of apple tree substantially as shown and described, characterized particularly as to novelty by the unique combination of earlier ripening than parent "Starkspur Red Rome Beauty" with early overall color of fruit a solid red, sugar content one-percent greater on the average than parent, good keeping qualities, mildew and insect resistant similar to parent, and somewhat less compact tree size than parent.

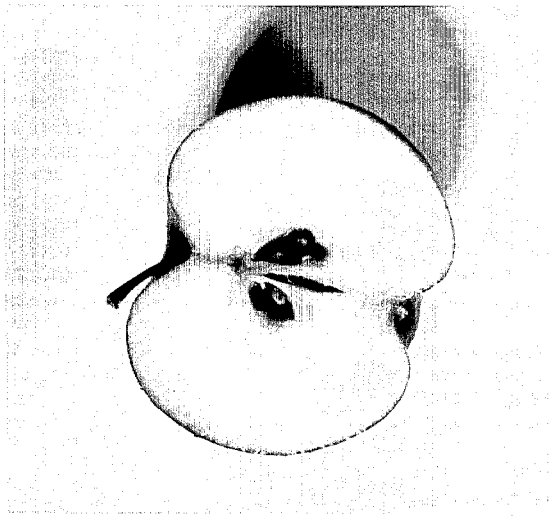
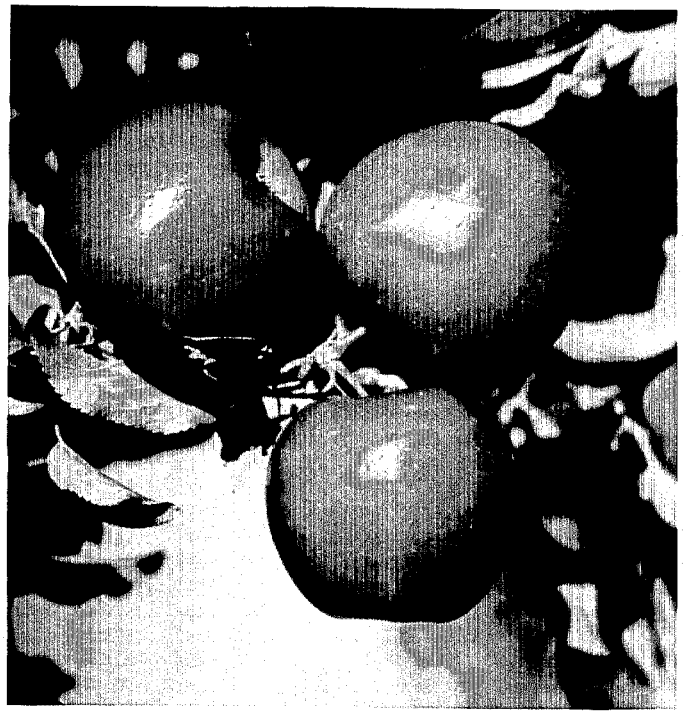
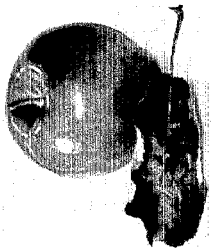

* * * * *